(12) United States Patent
Deans et al.

(10) Patent No.: US 11,726,093 B2
(45) Date of Patent: Aug. 15, 2023

(54) GAS SENSING IDENTIFICATION

(71) Applicant: C2Sense, Inc., Cambridge, MA (US)

(72) Inventors: Robert Deans, Grafton, MA (US); John Benjamin Goods, Woburn, MA (US); Alexander Robertson Petty, Watertown, MA (US); Jan Markus Schnorr, Cambridge, MA (US); Timothy Manning Swager, Newton, MA (US); Travis Matthew Theis, Cambridge, MA (US); Laura Jane Tschiegg, Somerville, MA (US); Joseph J. Walish, West Roxbury, MA (US); Nicole Katheryn Keller, Cambridge, MA (US)

(73) Assignee: C2Sense, Inc., Watertown, MA (US)

( * ) Notice: Subject to any disclaimer, the term of this patent is extended or adjusted under 35 U.S.C. 154(b) by 361 days.

(21) Appl. No.: 16/778,418

(22) Filed: Jan. 31, 2020

(65) Prior Publication Data
US 2020/0249237 A1    Aug. 6, 2020

Related U.S. Application Data

(60) Provisional application No. 62/799,540, filed on Jan. 31, 2019.

(51) Int. Cl.
*G01N 33/58* (2006.01)
*G01N 27/12* (2006.01)

(52) U.S. Cl.
CPC .......... *G01N 33/58* (2013.01); *G01N 27/127* (2013.01)

(58) Field of Classification Search
CPC .............................. G01N 27/127; G01N 33/58
See application file for complete search history.

(56) References Cited

U.S. PATENT DOCUMENTS

| 8,153,435 | B1 | 4/2012 | Fraser |
| 8,802,447 | B2 | 8/2014 | Swager et al. |
| 9,841,344 | B2 | 12/2017 | Rabb et al. |

(Continued)

FOREIGN PATENT DOCUMENTS

WO    WO 2017/189428 A1    11/2017

OTHER PUBLICATIONS

Invitation to Pay Additional Fees dated Apr. 2, 2020 for Application No. PCT/US2020/016058.

(Continued)

*Primary Examiner* — Jennifer Wecker
*Assistant Examiner* — Kathryn Elizabeth Limbaugh
(74) *Attorney, Agent, or Firm* — Wolf, Greenfield & Sacks, P.C.

(57) ABSTRACT

Components, systems, and methods for gas sensing identification are generally disclosed. In some embodiments, a characteristic of an article (e.g., identity, authenticity, property, product associated information such as age or quality, etc.) may be determined by determining the presence (e.g., an amount) or absence of a chemical compound (or compounds) emanating from the article. For example, the presence or absence of the compound (or compounds) emanating from the article identifies a characteristic of the article. In some embodiments, the chemical compound(s) has been proactively added to the article. That is to say, in some embodiments, the chemical compound is not inherently associated with the article but is added in order to, for example, identify a characteristic of the article.

7 Claims, 4 Drawing Sheets

(56) References Cited

U.S. PATENT DOCUMENTS

2005/0241989 A1  11/2005  Sant et al.
2013/0096030 A1   4/2013  Jeppesen et al.
2017/0322103 A1  11/2017  Rabb et al.
2017/0322167 A1  11/2017  Swager et al.

OTHER PUBLICATIONS

International Search Report and Written Opinion dated May 26, 2020 for Application No. PCT/US2020/016058.
International Preliminary Report on Patentability dated Aug. 12, 2021 for Application No. PCT/US2020/016058.
Zhang et al., Functionalization of Single-Walled Carbon Nanotubes and Fullerenes via a Dimethyl Acetylenedicarboxylate-4-Dimethylaminopyridine Zwitterion Approach. J Am Chem Soc. 2007;129(25):7714-5.
Partial European Search Report dated Oct. 26, 2022 for Application No. EP 20748029.4.
Extended European Search Report dated Jan. 31, 2023 for Application No. EP 20748029.4.

GAS SENSING IDENTIFICATION

RELATED APPLICATIONS

This application claims priority under 35 U.S.C. § 119(e) to U.S. Provisional Application Ser. No. 62/799,540 filed on Jan. 31, 2019, which is hereby incorporated by reference in its entirety for all purposes.

FIELD OF THE INVENTION

Embodiments described herein generally relate to gas sensing identification such as detection of analytes for determining a characteristic of an article.

BACKGROUND OF THE INVENTION

Gas sensing technology is being used in a wide variety of applications such as safety, security, process monitoring and air quality control. However, many such gas sensors are limited by complex manufacturing processes, low sensitivity, and/or false indications of detection. As such, the applications of such gas sensors are often limited. Accordingly, improved methods and systems are needed.

SUMMARY OF THE INVENTION

Components, systems, and methods for gas sensing identification are generally disclosed.

In one aspect, methods are provided. In some embodiments, the method comprises determining the presence or absence of a chemical compound or multiple compounds in the gas phase emanating from an article to which the compound or compounds have been proactively added, wherein the presence or absence of the compound or compounds identifies a characteristic of the article.

In some embodiments, the method comprises determining an amount of a chemical compound in the gas phase emanating from an article to which the compound has been proactively added, wherein the concentration of the chemical compound identifies a characteristic of the article.

In some embodiments, the method comprises triggering the release of a chemical tag deposited on a label, the label associated with the article, or the chemical tag deposited directly on the product, detecting, using a gas sensor, the presence or absence of an analyte or analytes associated with the chemical tag, thereby identifying the characteristic of the article.

In some embodiments, the chemical tag is non-volatile prior to triggering.

In some embodiments, the method comprises positioning a sensor proximate an article suspected of containing a chemical tag, detecting, using the sensor, the presence of the chemical tag, and determining, if the chemical tag is present, a characteristic of the article, wherein the chemical tag is not inherently associated with the article and wherein the sensor comprises a plurality of carbon nanotube-based chemiresistors.

In some embodiments, the method comprises determining a first ratio of an amount of a first chemical compound to an amount of a second chemical compound, each compound in a gas phase, emanating from an article under a first set of conditions, and determining a second ratio of an amount of the first chemical compound to an amount of the second chemical compound emanating from the article under a second set of conditions different than the first set of conditions, wherein the first chemical compound and the second chemical compound have each been proactively added to the article and wherein the change between the first ratio and the second ratio identifies a characteristic of the article.

In another aspect, labels are provided. In some embodiments, the label comprises means for associating the label with an article, and a chemical tag comprising a plurality of identifiable analytes, wherein a vapor signature of the plurality of identifiable analytes identifies a characteristic of the article, wherein the chemical tag is not inherently associated with the object.

In some embodiments, the label comprises a marker comprising an optical barcode, watermark, hologram, RFID, invisible ink, dyes, colorimetric markers, fluorescent markers, nanoparticles, nanorods, quantum dots, antibodies, proteins, and/or nucleic acids.

In some embodiments, the plurality of identifiable analytes comprises two or more types of functional groups within one or multiple molecules.

In some embodiments, the chemical tag is applied at a plurality of spatially-distinct locations.

In yet another aspect, sensors are provided. In some embodiments, the sensor comprises a detector capable of detecting a tag on a substrate using gas sensing, wherein the substrate is configured to be positioned proximate an article, wherein the detector, if the tag is present, is configured to identify the article, and wherein the tag is not inherently associated with the article and wherein the sensor comprises a plurality of carbon nanotube-based chemiresistors.

In yet another aspect, systems are provided. In some embodiments, the system comprises a chemical tag proactively associated with the article, optionally, a label associated with the article, the label comprising a chemical tag, a sensor configured to determine the presence of the chemical tag using gas sensing after triggering the release of the chemical tag, and a detector configured to identify a characteristic of the article if the sensor detects the release of the chemical tag, wherein the chemical tag is not inherently associated with the article.

In some embodiments, the chemical tag comprises of non-volatile compounds prior to triggering.

In some embodiments, the chemical tag has a non-zero vapor pressure after triggering.

In some embodiments, the triggering comprises the application of heat, light, chemical stimuli, pressure, ionizing radiation, moisture, or combinations thereof.

In some embodiments, the system comprises a detector comprising a gas sensing component and a label associated with the article, the label comprising a chemical tag, wherein the detector is configured to determine the presence or absence of the chemical tag, wherein the detector signals a characteristic of the article upon exposure to the chemical tag, and wherein the chemical tag is not inherently associated with the article.

In some embodiments, the system comprises a detector comprising a gas sensing component and a chemical tag associated with the article, wherein the detector is configured to determine the concentration of one or more chemical compounds associated with the chemical tag, wherein the detector signals a characteristic of the article upon exposure to the chemical tag, and wherein the chemical tag is not inherently associated with the article.

In some embodiments, the detector is configured to determine a rate of release of one or more chemical compounds associated with the chemical tag.

In some embodiments, the sensor comprises a plurality of carbon nanotube-based chemiresistors.

In some embodiments, the characteristic corresponds to product identification, authentication, point of origin, track & trace diversion of goods, counterfeit identification, adulterated product identification, product age, product quality, and/or legal document authentication of the article.

In some embodiments, the label comprises a second identifiable component.

In some embodiments, the second identifiable component comprises an optical barcode, hologram, watermark, RFID, invisible ink, dyes, colorimetric markers, fluorescent markers, nanoparticles, nanorods, quantum dots, antibodies, proteins, nucleic acids, or combinations thereof.

In some embodiments, the chemical tag comprises a nitro and/or siloxane functional group, an acid, a base, an amine, an alkene, a nitroaromatic, an oxide of nitrogen, a radical, a dihalide, $N_2O$, peroxide, and/or $CO_2$.

In some embodiments, the chemical tag does not comprise a volatile molecule.

In some embodiments, the chemical tag comprises a plurality of unrelated analytes.

In some embodiments, triggering the chemical tag comprises the application of heat, electromagnetic radiation, ultrasonic, mechanical force, pressure, electric fields, ionizing radiation, magnetic fields, a reactive chemical, or combinations thereof.

In some embodiments, the chemical tag is configured for instantaneous release from the label.

In some embodiments, the chemical tag is configured for time-dependent release from the label.

In some embodiments, the label comprises a plurality of chemical compounds.

In some embodiments, the chemical tag is activated or degraded by the presence of water, reactive chemicals, or excessive temperature.

In some embodiments, the label comprises a first chemical compound having a first vapor pressure and a second chemical compound having a second vapor pressure, the second vapor pressure is less than the first vapor pressure.

In some embodiments, the chemical tag comprises a photoacid or photobase generator.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

Figure 1A:
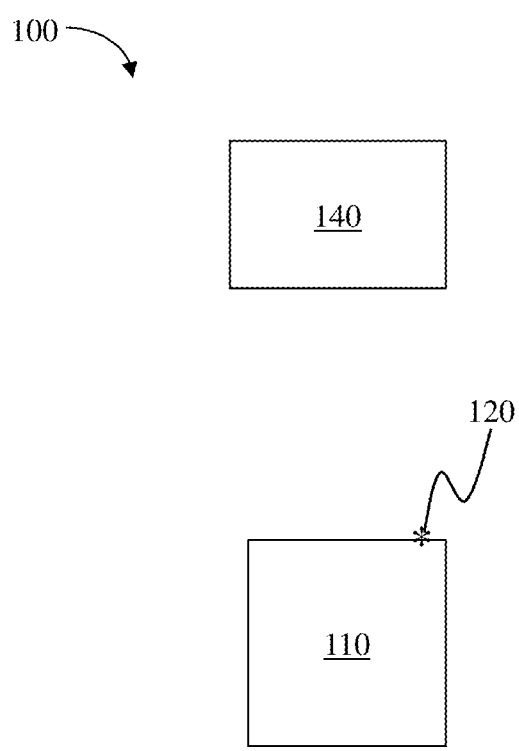
FIG. 1A is a schematic diagram of an article and a chemical tag associated with the article, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Components, systems, and methods for sensing identification (e.g., gas sensing and/or particle sensing) are generally disclosed. In some embodiments, a characteristic of an article (e.g., identity, authenticity, property, adulteration, product associated information such as age or quality, etc.) may be determined by determining the presence (e.g., an amount) or absence of a chemical compound(s) (i.e. analyte(s)) emanating from the article. For example, the presence or absence of the compound (or compounds) emanating from the article identifies a characteristic of the article. In some embodiments, the chemical compound(s) has been proactively added to the article. That is to say, in some embodiments, the chemical compound is not inherently associated with the article but is added in order to, for example, identify a characteristic of the article. In some embodiments, a label may be associated with the article. In some embodiments, the chemical compound is inherently associated with the article but is not present in an amount desirable for implementation of the invention, thus more is added for this purpose. In some embodiments, the chemical compound(s) are associated with the label such that the presence or absence of the chemical tag on the label identifies a characteristic of the associated article.

By way of an illustrative example only, and not intending to be limited as such, in some embodiments, one or more chemical compounds (e.g., acetone, methanol, nitrobenzene, benzoic acid, furan, dihexylamine, aniline) may be proactively added to an article that does not inherently comprise such chemical compounds (or, as noted above, may comprise such compounds but the additional of more facilitates the invention described herein). In some embodiments, the detection by a sensor of at least one of the one or more chemical compounds may identify a characteristic of the article. For example, two chemical compounds may be proactively added to the article. Detection, by a sensor, of both of the two chemical compounds may indicate the authenticity of the article. By contrast, a sensor which detects zero or one of the two chemical compounds may indicate that the article is not authentic. Those of ordinary skill in the art would understand, based upon the teachings of this specification, that the presence (or absence) of one or more chemical compounds associated with the article may identify one or more characteristics of the article as described in more detail herein (e.g., age, quality, origin, identity, etc.).

In some embodiments, the chemical tag comprises the one or more chemical compounds as described herein. In some embodiments, the chemical tag comprises one or more, two or more, three or more, four or more, five or more, six or more, seven or more, eight or more, nine or more or ten or more chemical compounds. In some embodiments, detection of the presence (or absence), of at least one of the one or more (or two or more, etc.) chemical compounds in the chemical tag identifies a characteristic of the article. For example, in some embodiments, detection of all of the chemical compounds present in the chemical tag identifies the characteristic of the article. In some embodiments, detection of at least a portion of the chemical compounds present in the chemical tag identifies the characteristic of the article. In some embodiments, the detection of none of the chemical compounds present in the chemical tag identifies the characteristic of the article. As described herein, detection may include measurement (e.g., by a sensor) of the presence (e.g., an amount, a concentration, a ratio), the absence, and/or the rate of release of one or more chemical compounds which may be used to identify one or more characteristics of the article. In some embodiments, the one or more chemical compounds may be delivered to the sensor in particulate form (e.g., particles comprising the chemical compound). In some embodiments, the one or more chemical compounds may be in a vapor phase.

In some embodiments, the chemical tag comprises a plurality of identifiable (e.g., by one or more sensors) chemical compounds (i.e. analyte). In some embodiments, a vapor signature of the plurality of identifiable analytes identifies the characteristic of the article. As described herein, in some embodiments, the chemical tag (and/or the one or more chemical compounds it comprises) is not inherently associated with the article. In some embodiments, the chemical tag may comprise one or more chemical compounds inherently associated with the article, but not present in an amount desirable for implementation of the systems and methods described herein, and thus more is added for this purpose. In some embodiments, the chemical tags described herein may be useful for additional applications. For example, in some embodiments, the chemical tag may be associated with an ink, a preservative, a flavoring, a fragrance, a colorant (e.g., a dye), and/or a structural element (e.g., glue, tape, strapping, packaging) associated with the article (or label).

In some embodiments, the plurality of identifiable chemical compounds comprise two or more types of functional groups within one or more chemical compounds. For example, a single compound may be associated with the article, the single compound comprising one or more (e.g., two or more, three or more, four or more) functional groups, wherein each functional group is detectable by one or more sensors. In some embodiments, the identification of one or more functional groups may identify a characteristic of the article.

The systems and methods described herein may be useful for a number of applications. For example, in some embodiments the systems and methods described herein may be used for product identification, product authentication, or the like. For example, in some embodiments, the characteristic of the article may include the identity of the article, point of origin of the article, the location of the article, the authenticity (or counterfeit nature) of the article, the quality of the article, the age of the article, whether the article is new or used, deterioration of the article, mishandling of the article, tampering of the article, or the like. Such characteristics may be useful for, for example, detecting theft, detecting unauthorized distribution, identifying illegal sales, identifying counterfeit products, identifying adulterated products, quality control, quality assurance, and tracking of the article.

As an illustrative embodiment, in some embodiments, the chemical tag may be used to detect degradation (e.g., a characteristic) of the article due to, for example, exposure to extreme temperatures, changes in moisture and/or humidity, exposure to light and/or chemical reactants). For example, in some such embodiments, the one or more compounds of the chemical tag may be released (e.g., triggered for release) and/or degraded by such temperatures, moisture, humidity, light, and/or reaction with particular chemicals. In some embodiments, the release under degradation of the one or more compounds may be detected thereby identifying the degradation (or other characteristic) of the article. In other cases the tag can in effect be used as a timer to ensure the quality of a material. For example, if the release of compounds is triggered by exposure to gamma radiation, ethylene oxide, or other sterilization agents as part of a sterilization process, then the tag can be used to indicate how much time has expired after this process. Similarly, a physical opening of packaging around an article and exposure to ambient atmosphere can be timed by release of compounds.

In some embodiments, a first portion of a first chemical compound is triggered to release under a first set of conditions and a second portion of the first chemical compound is triggered to release under a second set of conditions, different than the first set of conditions.

In some embodiments, a first portion of a first chemical compound is triggered to release under a first set of conditions and the first chemical compound is not released under a second set of conditions, different than the first set of conditions.

In some embodiments, a first portion of a first chemical compound is triggered to release under a first set of conditions at a first rate, and a second portion of the first chemical compound is triggered to release under a second set of conditions at a second rate, the first set of conditions being different than the second set of conditions and the first rate being different than the second rate.

In some embodiments, at least a portion of a first chemical compound is triggered to release under a first set of conditions and at least a portion of a second chemical compound is triggered to release under a second set of conditions, different than the first set of conditions.

In some embodiments, at least a portion of a first chemical compound and at least a portion of a second chemical compound is triggered to release under a first set of conditions. In some embodiments, the first chemical compound and/or the second chemical compound does not release under a second set of conditions, different than the first set of conditions.

In some embodiments, as described herein, changes in the release profile (e.g., amount, rate) of a chemical compound, or changes in the release profile (e.g., amount, rate, ratio) of two more chemical compounds, under a particular set(s) of conditions, corresponds to one or more characteristics of an article. That is to say, in some embodiments, one or more characteristics of an article may be identified based upon the release profile of one or more chemical compounds (e.g., chemical compounds proactively added to the article).

In some embodiments, the chemical tag may be applied to an article and a record of the characteristic of the article associated with that chemical tag may be made. For example, in some embodiments, the identity of the article may be confirmed if a particular chemical tag is detected by a detector.

The chemical tags described herein may be implemented in any suitable manner. For example, the chemical tag may be associated with a gas-emitting label. In some embodiments, the chemical tag and/or label may be single use or designed for multiple (e.g., repeated) use. In some embodiments, the chemical tag and/or label may be configured for slow release and/or triggered release of one or more compounds associated with the chemical tag, as described herein.

In some embodiments, the chemical tags described herein may be combined with one or more additional identifying components. For example, in some embodiments, a label may comprise a chemical tag (e.g. comprising one or more chemical compounds) and a second identifying component, different than the chemical tag. In some embodiments, a first label comprising the chemical tag and a second label comprising the identifying component may each be associated with an article. For example, in some embodiments, the chemical tag (or label) may be associated with a single or multidimensional optical barcode. Those of ordinary skill in the art would understand, based on the teachings of this specification, how to select additional identifying components for use with the chemical tags and systems described herein. In some embodiments, the article is associated with a chemical tag (or label comprising the chemical tag) and a second identifying component such as an optical barcode, hologram, RFID, and/or additional chemical markers and/or biological markers. Nonlimiting examples of additional chemical markers and/or biological markers that may be used in conjunction with the systems described herein include, but are not limited to, colorimetric dyes, fluorescent dyes, IR dyes, watermarks, nanoparticles, nanorods, quantum dots, antibodies, proteins, nucleic acids, and combinations thereof.

Turning now to the figures, as illustrated in FIG. 1A, in some embodiments, system 100 comprises an article 110 and a chemical tag 120 associated with article 110. In some embodiments, chemical tag 120 comprises one or more chemical compounds. In some embodiments, as described herein, the one or more chemical compounds may identify characteristic of article 110. In some embodiments, sensor 140 may be used to detect the presence (or absence) of chemical tag 120 and/or the one or more chemical compounds chemical tag 120 comprises. In some embodiments, chemical tag 120 may be positioned proximate, adjacent, or directly adjacent article 110.

The term "associated with" as used herein means generally held in close proximity, for example, a chemical tag associated with an article may be adjacent a surface of the article. As used herein, when a chemical tag is referred to as being "adjacent" a surface, it can be directly adjacent to (e.g., in contact with) the surface, or one or more intervening components (e.g., a label) may also be present. A chemical tag that is "directly adjacent" a surface means that no intervening component(s) is present. In some embodiments, the chemical tag is adjacent a surface of the article. In some embodiments, the chemical tag is directly adjacent a surface of the article. In some embodiments, the chemical tag is incorporated into the article (e.g., is present within the bulk of at least a portion of the article but, absent the addition of the chemical tag to the article, would not be inherently present in the article itself or not present in an amount desirable for implementation of the systems and/or methods described herein).

Figure 1B:
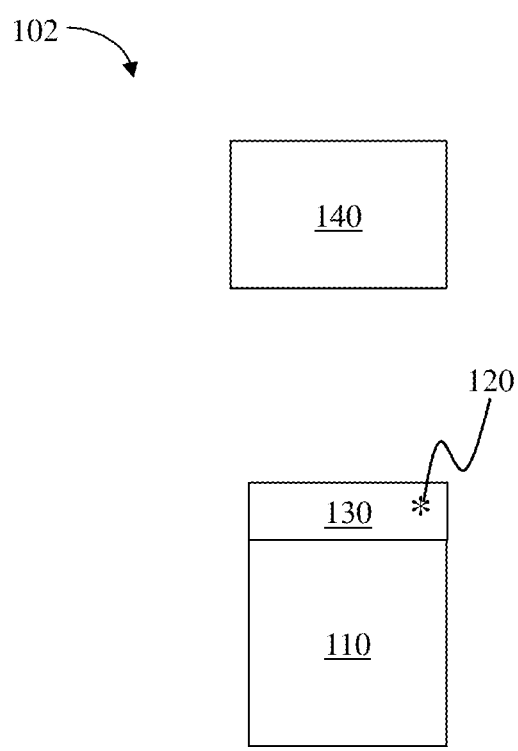
FIG. 1B is a schematic diagram of an article, a label, and a chemical tag associated with the label, according to one set of embodiments.

In some embodiments, the chemical tag is associated with the article and adjacent (e.g., directly adjacent) a label, the label associated with the article. For example, as illustrated in FIG. 1B, system 102 comprises article 110 and chemical tag 120 associated with article 110. In some embodiments, a label 130 is associated with article 110. In some embodiments, chemical tag 120 is associated with label 130. In some embodiments, label 130 comprises one or more compounds forming chemical tag 120. In some embodiments, the label is adjacent the article. In some embodiments, the label is directly adjacent (e.g., affixed to) the article. In some embodiments, the label is proximate the article but not necessarily adjacent the article. For example, in some embodiments, the label may be present in a container containing at least a portion of the article.

The term "label" as used herein is given its ordinary meaning in the art and generally refers to a component (e.g., comprising paper, fabric, plastic, ink, electronic device, or other material) associated with an article and giving information about said article. In an exemplary embodiment, the label is a sticker that contains functionality. In another exemplary embodiment, the label is a marker. In yet another exemplary embodiment, the label is a stamp. In other embodiments the label is printed or sprayed on an article. Other labels are also possible and means for associating labels with an article are described in more detail below.

In some embodiments, the chemical compound(s) passively emanates (e.g., releases) from the article (or label associated with the article). In some embodiments, the chemical compound does not emanate from the article and may be stimulated (e.g., triggered) to release from the article such that its presence (or absence) may be detected. In some embodiments, the chemical compound emanates from the article and stimulation (e.g., triggering) of the chemical compound increases the amount and/or rate of release of the chemical compound from the article. In some embodiments, the change in amount and/or rate of release of the chemical compound(s) identifies a characteristic of the article. In some embodiments, a change in the ratio of the amount of two or more chemical compounds identifies a characteristic of an article. In some such embodiments, the change in the ratio may be determined by measuring a first ratio of an amount of a first chemical compound to an amount of a second chemical compound under a first set of conditions and measuring a second ratio of an amount of the first chemical compound to an amount of the second chemical compound under a second set of conditions different than the first set of conditions, wherein the change between the first ratio and the second ratio identifies a characteristic of the article.

For example, in some embodiments, each chemical compound may be stimulated in such a way that the rate of release (or amount) of each chemical compound from the article (or the label associated with the article) increases (or deceases). In some such embodiments, the change in the rate of release and/or change in amount released of each chemical compound(s) may correspond to a characteristic of the article. By way of example, and without wishing to be limited as such, in some embodiments, a particular first rate of release (e.g., zero, non-zero) detected may indicate that the article is authentic. By contrast, a second rate of release (e.g., zero, non-zero), different than the first rate of release, if detected may indicate that the article is not authentic. In some embodiments, a single triggered release will result in substantially all (e.g., greater than or equal to 90 vol % and less than or equal to 100 vol %, greater than or equal to 95 vol % and less than or equal to 100 vol %, greater than or equal to 98 vol % and less than or equal to 100 vol %, greater than or equal to 99 vol % and less than or equal to 100 vol %) of the chemical compound being released (e.g., into the atmosphere) versus the total amount of chemical compound associated with the article. In some embodiments, at least a portion of the chemical compound is released (e.g., upon triggering, passively over time). For example, in some embodiments, greater than or equal to 1 vol %, greater than or equal to 2 vol %, greater than or equal to 5 vol %, greater than or equal to 10 vol %, greater than or equal to 15 vol %, greater than or equal to 20 vol %, greater than or equal to 30 vol %, greater than or equal to 40 vol %, greater than or equal to 50 vol %, greater than or equal to 60 vol %, greater than or equal to 70 vol %, greater than or equal to 80 vol %, or greater than or equal to 85 vol % of the chemical compound is released versus the total amount of chemical compound associated with the article. In some embodiments, less than or equal to 90 vol %, less than or equal to 85 vol %, less than or equal to 80 vol %, less than or equal to 75 vol %, less than or equal to 70 vol %, less than or equal to 60 vol %, less than or equal to 50 vol %, less than or equal to 40 vol %, less than or equal to 30 vol %, less than or equal to 20 vol %, less than or equal to 15 vol %, less than or equal to 10 vol %, less than or equal to 5 vol %, or less than or equal to 2 vol % of the chemical compound is released versus the total amount of chemical compound associated with the article. Combinations of the above-referenced ranges are also possible (e.g., greater than or equal to 1 vol % and less than or equal to 90 vol %). Other ranges are also possible.

In some embodiments, a plurality of triggered releases (e.g., sequential triggered releases, periodic triggered releases) results in at least a portion of the chemical compound to be released. In an exemplary embodiment, multiple triggered releases may be useful for repeated authentication of the article. In some embodiments, the chemical compound may be released over a particular period of time such that the intensity of the signal produced by the sensor in response to the chemical compound (e.g., indicating amount, concentration, ratio of chemical compounds, etc.) may be monitored over time. In some such embodiments, the release profile of the chemical compound may be used to determine a characteristic of an article (e.g. authenticity, freshness, whether the item had been used, etc.) In some embodiments, a plurality of triggered releases of one or more chemical compounds in a particular order may be used to generate, for example, a complex identifiable signal such that the time-domain of the identifiable signal corresponds to a characteristic of the article (e.g., identity, authenticity, etc.). Those of ordinary skill in the art would understand, based upon the teachings of this specification, that the rate of release and/or release profile may identify another characteristic of the article as described in more detail herein (e.g., age, quality, origin, identity, etc.).

The chemical tags and labels described herein may be applied to the article on any suitable manner. For example, in some embodiments, the chemical tag and/or label may be applied at one or more (e.g., two or more, three or more, four or more, five or more) or at a plurality of spatially distinct locations. For example, in some embodiments, the article comprises one or more (or two or more, etc.) chemical tags, wherein each chemical tag is the same or different. In some embodiments, each chemical tag may identify a same or different characteristic of the article.

Generally, any chemical reaction that gives a volatile product can be used to create a signature that can be detected. In some embodiments, the detector (e.g., sensor) is a chemiresistive device. In some embodiments, the detector may be configured to detect changes in an intensity and/or wavelength of electromagnetic radiation (e.g., fluorescence). In some embodiments, the detector may be configured to detect a change in the resonant frequency of a device overcoated by a selector material. In some embodiments, the detector may be configured to detect a change in color, a number of particles, a particle size distribution, a molecular weight of a compound, thermal conductivity, and/or light absorption, scattering, and/or transmission. In some embodiments, as described herein, more than one chemical compound may be released to create a unique identifier of an article.

Non-limiting examples of chemical compounds include acetone, methanol, nitrobenzene, furan, dihexylamine, aniline, nitromethane, benzene, toluene, o-xylene, m-xylene, p-xylene, mesitylene, nitrobenzene, phenols, anilines, quinones, halogens, hydrogen, carboxylic acids, acrylates, alkenes, cyano-aromatics, hexane, hexene, hexenal, ethylene, 1-methylcyclopropene, propene, butenes, isoprene, cyclohexanone, acetone, tetrahydrofuran (THF), methanol, ethanol, isopropanol, hexanal, DMMP, acetonitrile, nitromethane, ethyl acetate, methyl acetate, water, dimethyformamide (DMF), formaldehyde, dimethylsulfide, ethylene, peroxide, and ammonia.

In some embodiments, the chemical compound is an odorant or scent. However, in some embodiments, the chemical compound is not a scent (e.g., lavender, peach, peppermint, etc.). In some embodiments, the chemical compound is a flavoring or colorant (e.g., ingestible dye).

In some embodiments, the chemical compound may be selected to have a suitable vapor pressure. In some embodiments, the chemical compound may be selected based upon its interaction with an environmental condition (e.g., heat, moisture, humidity, light). In some embodiments, the chemical compound may be selected based upon its reaction with a particular reactant. For example, in some embodiments, a reactant may be used to trigger the release of the compound from the label and/or article such that a characteristic of the article may be identified. Other chemical compounds are also possible and such suitable compound(s) may be used with the systems and methods described herein and one of ordinary skill in the art would understand how to select such compounds based upon the teachings of this specification.

In some embodiments, the chemical compounds described herein may be readily detected at trace levels that can range from parts per thousand to parts per billion. In some embodiments, the chemical tag comprises one or more compounds, wherein each compound may be released simultaneously. In some embodiments, each compound may be released at different times (e.g., depending upon vapor pressure and/or other conditions). In some embodiments, each compound may have the same or different rate of release (e.g., without triggering, after triggering).

In some embodiments, each compound of the chemical tag may be volatile or non-volatile. For example, in some embodiments, a first compound may be selected such that it is volatile and passively releases (e.g., emanates) from the article. Such compounds may be useful for, for example, determining if the article has passed its shelf life. In some embodiments, a second compound, the same or different from the first compound, may be selected such that it is non-volatile and may be triggered to be released (e.g., emanate) from the article such that it may be detected by a sensor.

In some embodiments, the compound comprises a particular functional group (e.g., an oxidizing or a reducing functional group). In an exemplary embodiment, the functional group is a nitro group or a siloxane group.

In some embodiments, the chemical tag may be selected such that it otherwise produces a false positive in some certain commercially available gas sensors. That is to say, in some embodiments, the systems described herein may comprise a chemical tag comprising a chemical compound that would generally be misidentified by commercially available sensors thus generating a false positive. By contrast, in some embodiments, the sensors and systems described herein are configured to identify the presence or absence of the specific chemical compound(s). Without wishing to be bound by theory, in some embodiments, a nitro group and/or siloxane group (or other functional group) may generate false positives and/or interfere with traditional gas sensors (e.g., thus generating a false positive). In some embodiments, the sensors and/or detectors described herein do not produce a (false) positive identification of one or more chemical compounds in the presence of a nitro group and/or siloxane group.

In some embodiments, the chemical tag may be triggered such that one or more chemical compounds are released (e.g., such that the one or more chemical compounds may be detected by a sensor proximate the chemical tag). The chemical compound(s) may be released using any suitable means. For example, in some embodiments, at least a portion of the one or more chemical compounds are released upon the application of heat, electromagnetic radiation, ultrasonic, mechanical forces (e.g., scratching, twisting, bending, pressure), electric fields, magnetic fields, chemical reactants, or combinations thereof. In an illustrative embodiment, the chemical tag may be exposed to one or more types of triggering (e.g., releasing one or more chemical compounds of the chemical tag). For example, the chemical tag may be exposed to a first wavelength of electromagnetic radiation, then exposed to a second wavelength of electromagnetic radiation, and then, optionally, heated, wherein each exposure step releases at a least a portion of one or more chemical compounds on the chemical tag. In some embodiments, the detection of the release (or absence thereof) of each chemical compound in a particular manner identifies a characteristic of the article. Other combinations of triggering steps are also possible.

In some embodiments, the chemical tag may be triggered via exposure to a chemical reactant. Non-limiting examples of suitable chemical reactants include those discussed in the prophetic example below. In some embodiments, the chemical reactant comprises a photoacid or photobase generator.

In some embodiments, two or more different chemical compounds may be used to create a unique chemical signature for identification of a characteristic of the article. For example, the presence of a first chemical compound and the presence of a second chemical compound (each compound not inherently associated with the article e.g., proactively added to the article) may together identify a characteristic of the article.

For example, exposure to sunlight and the associated UV radiation could be measured by the depletion of one chemical tag or the photochemical activation of another chemical tag. In some embodiments, as described herein, multiple chemical tags may be used to provide more detailed information. Similar methods could be used to monitor collective humidity exposure of a product. In some embodiments, a chemical tag could be decomposed or generated by the exposure to water vapor or liquid. For certain applications, chemical tags may be selected that respond to certain chemicals. For example, if food were treated with peroxides or bleach to neutralize bacteria, a tag could be placed that would have indicated the prior exposure or ideally validate that the material had no exposure to these chemicals.

In an exemplary embodiment, a chemical tag comprises a volatile compound (e.g., peroxide) mixed with a binding agent, such as a hydrophilic polymer. Hydrophilic polymers include, but are not limited to, polyvinyl alcohol, polyvinylpyrrolidone, and polyacrylic acid. Other binding agents are also possible. The volatile compound may be added at any suitable weight loading ratio (e.g., greater than or equal to 1 wt % and less than or equal to 12 wt % versus the total weight of the chemical tag). In some embodiments, the chemical tag is deposited upon the surface of an article. The article may, in some cases, be allowed to dry at atmospheric temperature and pressure or under reduced pressure (e.g., vacuum). In some embodiments, the labeled article is associated with an appropriate gas sensor to detect the presence of the volatile peroxide.

Such embodiments need not be limited to reactive chemical(s). In some embodiments, an inert gas such as methane or $CO_2$ could be used to activate or release a chemical compound. For example, in an exemplary embodiment, methane could plasticize a material that allows for greater diffusion of molecules thought it. Such enhanced transport could result in increased depletion. In some embodiments, a material bearing amines could be developed that either enhances or attenuates a chemical tag upon generation. Without wishing to be bound by theory, $CO_2$ may be an indicator for microbial activity and may be used, in some cases, to evaluate the status of a material. Similar methods are possible for thiols or amines that are also associated with microbial activity.

The chemical tags may be imagined for many other methods, including cumulative exposure to molecular oxygen, nitrogen oxides ($NO_x$), or radiation. Physical changes in materials need not be limited to chemical triggers and thermal methods may be applied.

In some embodiments, the chemical compound may exhibit a particular identifiable phase change behavior under a particular set of conditions that may identify a characteristic of an article. For example, and without wishing to be bound by theory, a polymer below its glass transition temperature, it is in a dense state with reduced dynamics of the polymer chains. In the glass phase of the polymer chemical tags may have reduced mobility. However, at the glass transition temperature segmental dynamics in the polymers become active and an increase in the free volume is observed. In some embodiments, such dynamics and free volume may enhance chemical tag diffusion and may be used to trigger a chemical tag release at a very specific temperature. In some cases, this may be used to monitor the thermal history of a product or article. In some embodiments, multiple polymers with different glass transition temperatures may be used e.g., to provide a thermal history of the article.

Chemical tags may be designed to respond to lower temperatures as well as elevated temperatures. Combinations of materials with different coefficient of expansion or temperatures for phase changes may be combined, in some cases, that produce pores or phase separation processes. In some embodiments, the chemical tags may be released by enhanced diffusion of a reacting species. An increased diffusion of a molecular acid in a material may, in some cases, result in a bimolecular reaction with the chemical tag precursor and thereby result in the generation of a chemical tag signal. In some embodiments, processes may result in exposure to moisture, air, and/or light if a phase change results in the change in the optical opacity or absorption of the material. In some embodiments, the processes described herein may be reversible or irreversible.

In some embodiments, the methods and systems described herein may utilize a sequential release of two or more compounds to identify one or more characteristics of an article.

In some cases, it may be desirable to have chemical tags that may be read for months or even years. In some embodiments, chemical reactions that occur in response to an added reactant, light, heat, radiation, or mechanochemical stimulus may be used. For example, chemical tag precursors may comprise ionic compounds that have effectively no vapor pressure allowing them to persist for years and the activation process to produce volatile chemical tags may involve the conversion to uncharged materials with volatility allowing for detection.

In some embodiments, a chemical tag has a latency in a physical packaging. For example, a barrier overcoating may be applied that prevents a chemical tag or chemical tag precursor from evaporating of being capable of activation to generate a vapor. Such an overcoating could be as simple as a barrier polymer that is peeled or scratched off of an article. In some embodiments, the overcoating could be made porous through thermal, photochemical, chemical, and/or mechanical processes.

In some embodiments the chemical tag is associated with a porous material (e.g., a label comprising a porous material). In some embodiments, the pores of the porous material may encapsulate the chemical tag such that they may be switched between states that allow for permeation or block the diffusion of the chemical tag/chemical tag precursors from diffusing out of the pores. Chemical tag/chemical tag precursors and other materials may be, in some cases, deposited in multilayer structures that allow for sequential or simultaneous exfoliation/activation. Each layer may comprise one or more chemical compounds and may have different triggering/release mechanisms.

In some embodiments, the one or more chemical compounds of the chemical tag may be at least partially encapsulated. For example, in some embodiments, the chemical tag may be stimulated such that the release of the chemical compound(s) from encapsulation is triggered. In some embodiments, the chemical tag may be dispersed on colloids and then encapsulated by the polymerization of interfacial monomers or assembly of a barrier coating. Non-limiting examples of resulting capsules may range in size from structures that are the size of micelles (e.g., 5 nm in diameter) to large colloidal particles (e.g., 500 microns in diameter). Additional sizes are also possible.

In some embodiments, the chemical tag may be combined with one or more different materials. For example, polymerizations or polymer deposition may, in some cases, be used to form phase separation with polymers and thereby spontaneously form domains of a chemical tag or chemical tag precursor(s) with the polymer. The polymer may be inert and the chemical tag/chemical tag precursor may, in some cases, be released by mechanical disruption of the material. Alternatively, the polymer may be an active element and part of the triggered release, generation, or activation of the chemical tag. The polymer and chemical tag/chemical tag precursor and related elements may be deposited, in some cases, from solution onto a tag or made separately and applied in a lamination step. In some embodiments, the polymer can be produced in situ to make a film comprising the chemical tag. Those of ordinary skill in the art would understand, based upon the teachings of this specification, that the size and density of the chemical tag phase can be controlled by, for example, processing conditions, surfactants and the like. Crosslinking of the polymer host materials or the polymers encapsulants used in colloid production may be used, in some cases, to modulate the diffusion through these materials. Such crosslinks may be designed to be removed upon exposure to a chemical, photochemical, enzymatic, mechanical, electrochemical, or thermal process.

In some embodiments, the polymer is deformable such that deformation (e.g., stretching, bending) of the polymer releases the chemical compound(s) of the chemical tag.

Any suitable polymer may be used. For example, in some embodiments, the polymer may be kinetically stable (and thermodynamically unstable) such that it will generally spontaneously depolymerize with a bond rupture. An example of such a class of polymers are the poly(vinyl sulfones), which, without wishing to be bound by theory, when fragmented at room temperature will spontaneously depolymerize. Such materials have a broad compositional range and have generally been shown to be sensitive to radiation, base, electron transfer (redox), and thermal processes. Such polymers may be useful for the fabrication of polymer capsules comprising the chemical tags, described herein. Other polymers are also possible and those of ordinary skill in the art would be capable of selecting such polymers based upon the teachings of this specification.

The one or more chemical compounds may be applied to the article and/or label using any suitable means. Non-limiting examples of deposition methods include spray coating, dip coating, evaporative coating, ink jet printing, imbibing, screen printing, pad printing, gravure printing or lamination. In some embodiments, the one or more chemical compounds may be bound to the label or article via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus, nitrogen, carbon-nitrogen, metal-oxygen, or other covalent bonds. The hydrogen bond may be, for example, between hydroxyl, amine, carboxyl, thiol, and/or similar functional groups.

In some embodiments, the chemical tag need not be persistent and may slowly evaporate from a tag over time. Such a mechanism may also be used to provide for an expiration of a product and/or give an indication of the conditions upon which the object to be authenticated was exposed. For example, if a material has a cumulative thermal exposure, it could result in the depletion of one or more of the chemical compounds in the chemical tag. In some embodiments, identification of a characteristic of the article may also provide information about the status of the product.

In some embodiments, the chemical tag and/or label are edible. That is to say, in some embodiments, the chemical tag and/or label may be safely consumed by a subject (e.g., a human, an animal). Non-limiting examples of chemical compounds that may be used in the chemical tag (or label) include compounds listed in the Sigma-Aldrich Ingredients Catalog: Flavors & Fragrances (2014) and Sigma-Aldrich and the Sigma-Aldrich Flavor & Fragrance Ingredients Supplement (2018).

The labels described herein may comprise any suitable substrate for containing or otherwise associating the chemical tag with the article. For example, in some embodiments, the label may comprise a substrate, and a chemical tag (e.g. comprising one or more chemical compounds) associated with the substrate. Non-limiting examples of suitable substrates include silicone, silica, glass, metals, microporous materials, nanoporous materials, polymers, gels, and natural materials (e.g., paper, wood, rocks, tissues, hair, fur, leather).

In some embodiments, the label comprises a means for attaching the label to an article. Non-limiting examples of suitable means for attaching the label include adhesives, lamination, melt bonding, spray coating, spin coating, printing, strapping, and combinations thereof.

Any suitable type of sensor may be used to detect the presence (or absence) of a chemical tag (or one or more chemical compounds the chemical tag comprises). In some embodiments, the presence (or absence) of a chemical compound may be determined using a gas sensor. Although much of the description here relates to the use of gas sensors, in some embodiments, other sensors are also possible. For example, in some embodiments, one or more chemical compounds may be in particulate form. In some such embodiments, the sensor may be configured to detect the presence (or absence) of particles. Particles can be aggregates of a molecule of more complex heterogeneous materials with internal structure. The particle can deliver a chemical signal after being deposited on the sensor, or the particle can be the signal for authentication. For example, the particles could be charged and a sensor can detect them based on their charged structure. Alternatively, the particles could be active elements for electrical transport and change the conductance of a sensor material. The particles could also result in changes in optical properties such as color, fluorescence, light scattering, or other features. For example, in some embodiments, the presence (or absence) of a chemical compound may be determined using a sensor configured to detect particles. Those of ordinary skill in the art would be capable of selecting suitable sensors based upon the teachings of this specification.

In some embodiments, the sensor is positioned proximate an article suspected of containing a chemical tag. In some embodiments, upon detection of the compound(s), the sensor may be configured to send a signal. In some such embodiments, the signal may correspond to one or more characteristics of the article. As described herein, in some embodiments, the chemical tag (or the one or more chemical compounds the chemical tag comprises) are not inherent to the article. For example, in some embodiments, a sensor will not detect the presence (e.g., amount, concentration, non-zero rate of release) of a chemical compound adjacent an article unless the chemical compound had been proactively associated with the article prior to sensing.

In a particular set of embodiments, the detector (e.g., sensor) is a chemiresistive sensor. Typically, a chemiresistive sensor or the like may include a first electrode, a second electrode, and a sensor material arranged in electrical communication with the first and the second electrodes. Other configurations are also possible. The sensor material may include a conductive material (e.g., a plurality of conductive carbonaceous nanomaterial particles), such that resistance to current flow between the first and second electrode is affected by interaction of the sensor material. Upon exposure to a chemical compound, the chemical compound may interact with the sensor material to affect resistance to current flow between the first and second electrodes, thereby generating a signal in the device by which the chemical compound is determined. In some embodiments, the sensor material is in substantially a solid form. In some embodiments, the sensor material is in the form of a paste.

In some embodiments, the sensor comprises a plurality of conductive carbonaceous nanomaterial particles (e.g., carbon nanotubes) and a detector selected to selectively interact with a chemical compound of interest. In certain embodiments, the carbonaceous nanomaterial particles are carbon nanotubes. In some embodiments, the carbon nanotubes are single-walled nanotubes. In some embodiments, the carbon nanotubes are multi-walled nanotubes. In some embodiments, the carbon nanotubes are double-walled nanotubes. In some embodiments, the carbonaceous nanomaterial particles are selected from a group consisting of graphite powder, single-layer graphene, double-layer graphene, multi-layer graphene, reduced graphite oxide, and carbon black powder.

In some embodiments, the chemiresistive sensor comprises a plurality of functionalized nanoparticles. For example, thiol coated gold nanoparticles may be configured for use in identification of a characteristic of an article (e.g., authentication). In some embodiments, metal oxide nanoparticles and/or bulk metal oxide materials, optionally functionalized, may be configured for use in sensing of the chemical tag (e.g., for identification of a characteristic of an article). In some embodiments, one or more sensors (e.g., two or more sensors, three or more sensors, four or more sensors, a plurality of sensors) are used to identify one or more characteristics of an article. In some embodiments, the one or more sensors are configured to detect changes in resistance, frequency changes in a material or microcantilever, changes in a chemically sensitive transistor, changes in fluorescence, changes in refractive index, changes in color, changes in electrochemical potentials or currents, changes in the transparency of a material, swelling of a material, changes in the mechanical properties of a material, a characteristic response of a living organism, changes in reflected electromagnetic radiation, or combinations thereof.

In certain embodiments, the sensor comprises a selector (e.g., a selector molecule). The selector molecule may be any moiety that may interact with one or more chemical compounds and/or that may be responsive to a change in a surrounding medium or environment, and may be incorporated within the device in various configurations. For example, the detector may be a small molecule, a semiconductor device, an electrode, a nanoparticle, a MEMS device, a polymer, a biological species, or the like. In some embodiments, the selector may comprise ionic species (e.g., a salt). In some embodiments, the selector may comprise a neutral species. In some embodiments, the selector may be an organic, organometallic, or an inorganic species that behaves as a selector to provide specific responses. In certain embodiments, the selector may be attached to the carbonaceous nanomaterial particles via a covalent bond. In certain embodiments, the selector may be attached to the carbonaceous nanomaterial particles via a non-covalent bond. In certain other embodiments, the selector may be substantially contained within (e.g., dispersed within) the carbonaceous nanomaterial particles, and may not form a covalent bond to the carbonaceous nanomaterial particles.

In some embodiments, the selector may comprise a biological or a chemical group capable of binding another biological or chemical compound in a medium (e.g., solution, vapor phase, solid phase). For example, the selector may include a functional group, such as a thiol, aldehyde, ester, carboxylic acid, hydroxyl, and the like, wherein the functional group forms a bond with the chemical compound of interest. In some cases, the selector may be an electron-rich or electron-poor moiety wherein interaction between the chemical compound of interest and the detector comprises an electrostatic interaction.

In some embodiments, the interaction between the chemical compound of interest and the selector includes binding to a metal or metal-containing moiety. For example, in some embodiments, the selector may be a metal-containing species. For example, the species may be a metal-containing species, including metal salts. In some embodiments, the metal salt is a transition metal salt or complex. Some examples of metal salts include, but are not limited to, $TiO_2$, $TiCl_4$, and other titanium salts, $AgCl$, $AgPF_6$, $Ag(OCOCF_3)$, $Ag(SO_3CF_3)$, and other silver salts, $PtCl_2$ and other platinum salts, $Au_2Cl_6$ and other gold salts, $Al(OEt)_3$ and other aluminum salts, $Ni(SO_3CF_3)_2$, $NiCl_2$, and other nickel salts, $Cu(SO_3CF_3)$ and other copper salts, and $RhCl_3$ and other rhodium salts. In some embodiments, the species may be a copper-containing species. In some embodiments, the copper-containing species is a salt, such as a Cu(II) salt. In some embodiments, the species may be a palladium-containing species. In some embodiments, the palladium-containing species is a salt, such as a Pd(II) salt. Some examples of specific metal containing species include, but are not limited to, $PdCl_2$. In an exemplary embodiment, the selector comprises 5,10,15,20-tetraphenylporphyrinatocobalt(III) perchlorate ($[Co(tpp)]ClO_4$), 3,6-Di-2-pyridyl-1,2,4,5-tetrazine and combinations thereof.

In some embodiments, the carbonaceous nanomaterial particles are mixed with the detector in a ratio ranging from 3:1 to 1:10 by weight. In certain embodiments, the ratio of the carbonaceous nanomaterial particles to detector is 1:1 by weight. In certain other embodiments, the ratio of the carbonaceous nanomaterial particles to detector is 1:5 by weight. In certain other embodiments, the ratio of the carbonaceous nanomaterial particles to detector is 1:10.

In an exemplary set of embodiments, the sensor is a carbon nanotube-based chemiresistor sensor (e.g., comprising a plurality of carbon nanotube-based chemiresistors).

Figure 2A:
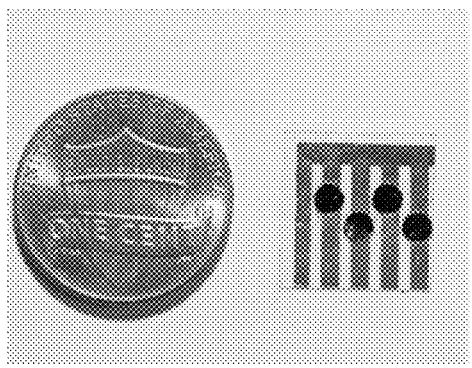
FIG. 2A is a photograph of an exemplary sensor for detecting a chemical tag, according to one set of embodiments.
Figure 2B:
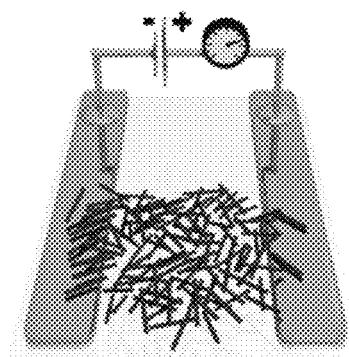
FIG. 2B is a diagram of an exemplary sensor for detecting a chemical tag, according to one set of embodiments.
Figure 3:
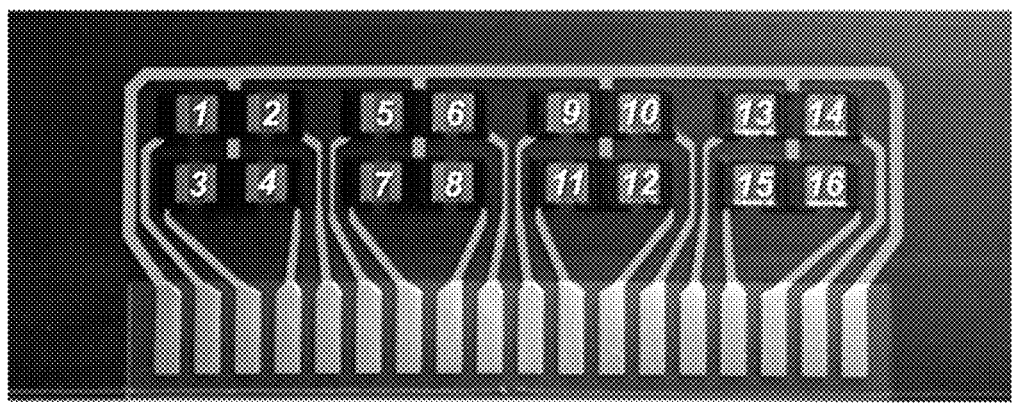
FIG. 3 is a photograph of an exemplary array of sensors for detecting one or more chemical tags, according to one set of embodiments.

In some embodiments, the sensor includes a first electrode and a second electrode; a sensor material disposed in electrical contact with the first and second electrode wherein, the sensor material includes, a plurality of conductive carbonaceous nanomaterial particles and a selector selected to selectively interact with a chemical compound of interest. The plurality of conductive carbonaceous nanomaterial particles and the selector are present in a mixture and, in some embodiments, the chemical compound can diffuse into the mixture to interact with the selector to change the conductivity of the mixture. The device further includes an electrical circuit capable of detecting the changes in the conductivity of the mixture to detect information regarding the chemical compound. FIGS. 2A-2B show an exemplary photograph (FIG. 2A) and diagram (FIG. 2B) of an exemplary sensor for detecting a chemical compound of interest in accordance with this disclosure.

In another aspect, the method of detecting a chemical compound includes providing a first electrode and a second electrode, providing a sensor material disposed in electrical contact with the first and second electrode, wherein the sensor material includes a plurality of conductive carbonaceous nanomaterial particles and a detector selected to selectively interact with a chemical compound of interest. The method further includes, in some embodiments, exposing the sensor material to the chemical compound, wherein the exposure to chemical compound changes the conductivity of the sensor material, and detecting the change in conductivity of the sensor material to gather information regarding the chemical compound (e.g., presence, amount, concentration, rate of release from the article and/or label).

In some embodiments, the first and second electrodes are located on a rigid substrate such as, glass or a polymeric material. In some other embodiments, the first and second electrodes are located on a printed circuit board. In some other embodiments, the first and second electrodes are located on a flexible substrate. In some embodiments, the flexible substrate is paper. In some other embodiments, the flexible substrate is a polymeric material. In some embodiments, the first and second electrodes are printed on the flexible substrate. The printing of the electrodes may be carried out using any of the common techniques known in the art. These techniques are, but not limited to, screen printing, off-set printing, gravure printing, block printing, inkjet printing, relief printing, pad printing and intaglio.

In some embodiments, the first electrode and the second electrode are part of a complex circuit such as, a Near Field Communication (NFC) or radio-frequency identification (RFID) chip.

In some embodiments, the chemical compound is a vapor and/or in a gas phase. In some embodiments, the chemical compound comprises a thiol, an ester, an aldehyde, an alcohol, an ether, an alkene, an alkyne, a ketone, an acid, a halide, a peroxide, a nitroaromatic, a base, or combinations thereof.

In some embodiments, the concentration of the chemical compound is in the range of 0 to 10%, 10 ppm to 10%, 100 ppm to 10%, 1000 ppm to 10%, 1 to 10%, or 5 to 10%. In some other embodiments, the concentration of the chemical compound is in the range of 0 to 5%, 10 ppm to 5%, 100 ppm to 5%, 1000 ppm to 5%, 1 to 5%, or 2 to 5%. In some other embodiments, the concentration of the chemical compound is in the range of 0 to 1%, 10 ppb to 1%, 100 ppb to 1%, 1 ppm to 1%, or 10 ppm to 1%. In some other embodiments, the concentration of the chemical compound is in the range of 0 to 1000 ppm, 10 ppb to 1000 ppm, 100 ppb to 1000 ppm, 1 ppm to 1000 ppm, or 10 ppm to 1000 ppm. In some other embodiments, the concentration of chemical compound is in the range of 0 to 100 ppm, 10 ppb to 100 ppm, 100 ppb to 100 ppm, 1 ppm to 100 ppm, or 10 ppm to 100 ppm. In some other embodiments the concentration of chemical compound is in the range of 0 to 80 ppm, 10 ppb to 80 ppm, 100 ppb to 80 ppm, 1 ppm to 80 ppm, or 10 ppm to 80 ppm. In some other embodiments the concentration of chemical compound is in the range of 0 to 50 ppm, 10 ppb to 50 ppm, 100 ppb to 50 ppm, 1 ppm to 50 ppm, or 10 ppm to 50 ppm. In some other embodiments the concentration of chemical compound is in the range of 0 to 10 ppm, 10 ppb to 10 ppm, 100 ppb to 10 ppm, or 1 ppm to 10 ppm. In some embodiments, the concentration of the chemical compound is in the range of 0 to 1 ppm, 10 ppb to 1 ppm, or 100 ppb to 1 ppm. In some other embodiments, the concentration of the chemical compound is in the range of 0 to 0.5 ppm, 10 ppb to 0.5 ppm, or 100 ppb to 0.5 ppm. In some other embodiments, the concentration of the chemical compound is in the range of 0 to 100 ppb, or 10 ppb to 100 ppb. In some other embodiments, the concentration of the chemical compound is in the range of 0 to 50 ppb, or 10 ppb to 50 ppb. In some other embodiments, the concentration of the chemical compound is in the range of 0 to 10 ppb.

The interaction between the chemical compound and the selector of the sensor material may include formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), and the like. The interaction may also comprise Van der Waals interactions. In one embodiment, the interaction comprises forming a covalent bond with a chemical compound. In some cases, the interaction between the device and the chemical compound may comprise a reaction, such as a charge transfer reaction. In some other embodiments, the species and/or another device component may undergo a chemical or physical transformation upon a change in the surrounding environment (e.g., change in temperature) to produce a determinable signal from the device. In some cases, the determinable signal is another chemical state of a material. The determinable signal may, in some cases, persist or subside over time.

The detector (or sensor material) may also interact with a chemical compound via a binding event between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of species include peptides, proteins, DNA, RNA, PNA.

In an illustrative embodiment, a metal electrode (e.g., gold) may be patterned, evaporated, or otherwise formed on the surface of a substrate (e.g., a glass substrate). A first layer containing the sensor material may be formed on the substrate, followed by a second layer formed on the first layer and containing the absorbent material.

"Electrical communication," as used herein, refers to materials that are in sufficient communication with each other, such that the transfer of electrons, polarons, excitons, and/or protons can occur between the two materials. For example, the first and second electrodes may not physically contact one another but may be in electrical communication with one another via the conductive material, such that upon application of a voltage or potential, a current flows from the one electrode through the conductive material to the other electrode.

As used herein, the term "carbon nanotube" is given its ordinary meaning in the art and refers to a substantially cylindrical molecule, in some cases, comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group. Carbon nanotubes may have a diameter of the order of nanometers and a length on the order of millimeters, resulting in an aspect ratio greater than about 100, greater than about 1000, greater than about 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

The carbon nanotubes may be functionalized or substituted with a wide range of functional groups. Examples of functional groups that carbon nanotubes may be substituted with include peptides, proteins, DNA, RNA, peptide nucleic acids (PNA), metal complexes, ligands for metals, ligands for proteins, antibodies, polarizable aromatics, crown ethers, hydroxyl amines, polymers, initiators for polymerizations, liquid crystals, fluorocarbons, synthetic receptors, and the like. The properties of the nanotubes may also be tailored based on the substitution of the fused, aromatic network. Those skilled in the art would recognize what types of functional groups would afford a particular, desired property, such as increased solubility, or the ability to determine an analyte.

Substituted carbon nanotubes may be synthesized using various methods, including those described in Zhang et al., J. Am. Chem. Soc. 2007, 129(25), 7714; International Publication No. WO2008/133779, which is incorporated herein by reference in their entirety for all purposes.

In some cases, the conductive material may comprise nanoparticles. As used herein, the term "nanoparticle" generally refers to a particle having a maximum cross-sectional dimension of no more than 1 µm. Nanoparticles may comprise inorganic or organic, polymeric, ceramic, semiconductor, metallic, non-metallic, magnetic, crystalline (e.g., "nanocrystals"), or amorphous material, or a combination of two or more of these. The nanoparticles may be also selected to be positively or negatively charged. Typically, nanoparticles may have a particle size less than 250 nm in any dimension, less than 100 nm in any dimension, or less than 50 nm in any dimension. In some embodiments, the nanoparticles may have a diameter of about 2 to about 50 nm. In some embodiments, the nanoparticles may have a diameter of about 2 to about 20 nm. The particle size may be measured by methods known in the art, such as electron microscopy.

Polymers or polymeric materials, as used herein, refer to extended molecular structures comprising a backbone (e.g., non-conjugated backbone, conjugated backbone) which optionally contain pendant side groups, where "backbone" refers to the longest continuous bond pathway of the polymer. In some embodiments, the polymer is substantially non-conjugated or has a non-conjugated backbone. In some embodiments, at least a portion of the polymer is conjugated, i.e. the polymer has at least one portion along which electron density or electronic charge can be conducted, where the electronic charge is referred to as being "delocalized." A polymer may be "pi-conjugated," where atoms of the backbone include p-orbitals participating in conjugation and have sufficient overlap with adjacent conjugated p-orbitals. It should be understood that other types of conjugated polymers may be used, such as sigma-conjugated polymers.

The polymer can be a homo-polymer or a co-polymer such as a random co-polymer or a block co-polymer. In one embodiment, the polymer is a block co-polymer. An advantageous feature of block co-polymers is that they may mimic a multi-layer structure, wherein each block may be designed to have different band gap components and, by nature of the chemical structure of a block co-polymer, each band gap component is segregated. The band gap and/or selectivity for particular analytes can be achieved by modification or incorporation of different polymer types, as would be understood by those of ordinary skill in the art. The polymer compositions can vary continuously to give a tapered block structure and the polymers can be synthesized by either step growth or chain growth methods.

The number average molecular weight of the polymer may be selected to suit a particular application. As used herein, the term "number average molecular weight (Mn)" is given its ordinary meaning in the art and refers to the total weight of the polymer molecules in a sample, divided by the total number of polymer molecules in a sample. Those of ordinary skill in the art will be able to select methods for determining the number average molecular weight of a polymer, for example, gel permeation chromatography (GPC). In some cases, the GPC may be calibrated vs. polystyrene standards. In some cases, the number average molecular weight of the polymer is at least about 10,000, at least about 20,000, at least about 25,000, at least about 35,000, at least about 50,000, at least about 70,000, at least about 75,000, at least about 100,000, at least about 110,000, at least about 125,000, or greater.

The sensor (e.g., a chemiresistive sensor) may also comprise an insulating material. The insulating material may be arranged between the conductive material and one or more electrodes and/or the substrate. Examples of suitable insulating materials include, but are not limited to, polysilicate glass, silicon dioxide, silicon nitride, and the like.

As used herein, the term "electrode" or "electrode material" refers to a composition, which, when connected to an electronic device, is able to sense a current or charge and convert it to a signal. An electrode may be comprised of a conductive material or combination of materials such as, for example, metals. Non-limiting examples of suitable metals include gold, copper, silver, platinum, nickel, cadmium, tin, and the like. The electrodes may also be any other metals and/or non-metals known to those of ordinary skill in the art as conductive (e.g. ceramics). The electrodes may be deposited on a surface via vacuum deposition processes (e.g., sputtering and evaporation), solution deposition (e.g., electroplating or electroless processes), or screen printing. In a specific example, gold electrodes are deposited by thermal evaporation. In another embodiment, gold electrodes are screen printed on a surface. The electrodes may, in some embodiments, comprise copper, silver, carbon, indium-tin oxide, or the like. The electrodes can also be produced from conducting polymers, carbon nanotubes, graphene, carbon, or combinations of these materials with metals.

As used herein, an "analyte" or "chemical compound" can be any chemical, biochemical, or biological entity (e.g. a molecule) to be analyzed. The analyte may be in vapor phase, liquid phase, or solid phase. In some embodiments, the analyte is a vapor phase analyte. In some cases, the analyte may be a form of electromagnetic radiation. In some cases, the analyte may be airborne particles. In some cases, the device may be selected to have high specificity for the analyte, and may be a chemical, biological, or explosives sensor, for example. In some embodiments, the analyte comprises a functional group that is capable of interacting with at least a portion of the device (e.g., a species). In some cases, the device may determine changes in pH, moisture, temperature, and the like, of a surrounding medium. The analyte may be a chemical species, such as an explosive (e.g., TNT), toxin, or chemical warfare agent. In a specific example, the analytes are chemical warfare agents (e.g., sarin gas) or analogs of chemical warfare agents (e.g., dimethyl methylphosphonate, DMMP).

In some embodiments, the chemical compound (i.e. analyte) may be an aromatic species, including optionally substituted aryl species and/or optionally substituted heteroaryl species, such as benzene, toluene, xylene, or polycyclic aromatic hydrocarbons such as benzo[a]pyrene. In some embodiments, the analyte may be an amine-containing species such as ammonia. In some embodiments, the analyte may be a nitrile-containing species such as acetonitrile. In some embodiments, the analyte may be an oxygen-containing species, such as a species comprising an alcohol, a ketone, an ester, a carboxylate, an aldehyde, other carbonyl groups, an ether, or the like. In some embodiments, the analyte may be a species comprising a ketone, an ester, an ether, or an aldehyde, such as cyclohexanone, ethyl acetate, THF, or hexanal. In some embodiments, the analyte is a phosphorus-containing analyte such as DMMP. In some embodiments, the analyte may be a nitro-containing species such as nitromethane or TNT. Other examples of analytes include alcohols, olefins, nitric oxide, thiols, thioesters, and the like.

In some cases, the sensor may determine changes in a condition, or set of conditions, of a surrounding medium. As used herein, a change in a "condition" or "set of conditions" may comprise, for example, change to a particular temperature, pH, solvent, chemical reagent, type of atmosphere (e.g., nitrogen, argon, oxygen, etc.), electromagnetic radiation, or the like. In some cases, the set of conditions may include a change in the temperature of the environment in which the sensor is placed. For example, the sensor may include a component (e.g., binding site) that undergoes a chemical or physical change upon a change in temperature, producing a determinable signal from the sensor.

As used herein, an "aromatic species" includes unsubstituted or substituted, monocyclic or polycyclic aromatic ring or ring radical, including unsubstituted or substituted monocyclic or polycyclic heteroaromatic rings or ring radicals (e.g., aromatic species including one or more heteroatom ring atoms). Examples of aromatic species include phenyl, naphthyl, anthracenyl, chrysenyl, fluoranthenyl, fluorenyl, phenanthrenyl, pyrenyl, perylenyl, and the like.

As used herein, "aryl" means a monocyclic or polycyclic-aromatic ring or ring radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl or alkyl substituted with one or more halo), hydroxy, alkoxy (preferably, lower alkoxy), alkylthio, cyano, halo, amino, and nitro.

As used herein, "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

Other embodiments suitable for use in the context of the embodiments described herein are described in International Pat. Apl. Serial No.: PCT/US2009/001396, filed Mar. 4, 2009, entitled, "Devices and Methods for Determination of Species Including Chemical Warfare Agents"; International Pat. Apl. Serial No.: PCT/US2009/006512, filed Dec. 11, 2009, entitled, "High Charge Density Structures, Including Carbon-Based Nanostructures and Applications Thereof"; U.S. patent application Ser. No. 12/474,415, filed May 29, 2009, entitled, "Field Emission Devices Including Nanotubes or Other Nanoscale Articles"; International Pat. Apl. Serial No.: PCT/US2011/051610, filed Oct. 6, 2010, entitled, "Method and Apparatus for Determining Radiation"; International Pat. Apl. Serial No.: PCT/US2010/055395, filed Nov. 4, 2010, entitled, "Nanostructured Devices including Analyte Detectors, and Related Methods"; International Pat. Apl. Serial No.: PCT/US2011/053899, filed Sep. 29, 2011, entitled, "COMPOSITIONS, METHODS, AND SYSTEMS COMPRISING POLY (THIOPHENES); International Pat. Apl. Serial No.: PCT/US2011/025863, filed Feb. 23, 2011, entitled, "Charged Polymers and Their Uses in Electronic Devices"; and International Pat. Apl. Serial No.: PCT/US2015/039971, filed Jul. 10, 2015, entitled "FORMULATIONS FOR ENHANCED CHEMIRESISTIVE SENSING", which applications are incorporated herein in their entireties for all purposes.

EXAMPLES

The following examples are intended to illustrate certain embodiments described herein, including certain aspects of the present invention, but do not exemplify the full scope of the invention.

Example 1—Passive Sensing Using Sensing System

The basic sensor element comprised a chemiresistive sensor chip. One sensor chip may be comprised of multiple sensing elements, and each element is comprised of a proprietary formulation of carbon nanotubes (CNTs), selectors for a specific response to a compound, and additives that are applied between two electrodes (FIGS. 2A-2B). The CNTs may be modified with selector molecules specific for the target analytes. Upon exposure to these analytes, the sensor produces an electrical response signal (i.e. a change in resistance) that is recorded and may be analyzed (e.g., by a computer, via the cloud). The nanotube network provides sensitivity toward the target analyte while maintaining excellent selectivity.

CNT sensor chips were placed in the sensor module and the resistances of the formulations were continuously recorded. Sensor chips were continuously exposed to ambient air via an active sampling method in which a piezoelectric pump draws air from an attached plastic tube. This air travels generally over the surface of the sensor chip. The sensor chips were exposed to individual small molecule volatile markers via the placement of a substrate saturated with the corresponding sample at the inlet of the device. The six volatiles markers used in this example were acetone, methanol, nitrobenzene, furan, dihexylamine, and aniline.

Table 1 summarizes the results for passive exposure to individual volatile analytes using the exemplary system. The varied response to multiple types of volatiles across numerous types of sensors demonstrated the ability to identify and use a volatile compound for, for example, article authentication. Table 1 shows the response of several sensors to six different volatile markers. Except for sensors I and J, each of the 10 sensors showed unique response profiles to the six analytes, providing a reasonable basis for deploying a 'barcode' type authentication device using this system. A check mark indicates that a measurable response, while an X indicates no measurable response was observed.

TABLE 1

| | Chip 1 | | | | | |
| --- | --- | --- | --- | --- | --- | --- |
| | Acetone | Methanol | Nitro-benzene | Furan | Dihexyl-amine | Aniline |
| Sensor A | ✓ | X | X | X | ✓ | ✓ |
| Sensor B | X | X | X | ✓ | X | X |
| Sensor C | ✓ | ✓ | X | ✓ | ✓ | ✓ |
| | Chip 2 | | | | | |
| | Acetone | Methanol | Nitro-benzene | Furan | Dihexyl-amine | Aniline |
| Sensor D | X | ✓ | X | ✓ | X | X |
| Sensor E | X | ✓ | X | X | X | X |

TABLE 1-continued

| | Acetone | Methanol | Nitro-benzene | Furan | Dihexyl-amine | Aniline |
|---|---|---|---|---|---|---|
| Sensor F | X | ✓ | X | ✓ | X | ✓ |
| Chip 3 | | | | | | |
| Sensor G | X | X | X | X | ✓ | ✓ |
| Sensor H | ✓ | ✓ | X | ✓ | ✓ | ✓ |
| Sensor I | ✓ | ✓ | X | X | ✓ | ✓ |
| Sensor J | ✓ | ✓ | X | X | ✓ | ✓ |

Example 2—Active Volatile Release of $CO_2$

The triggered release of a volatile agent was also performed. Pivalic acid is generally a carboxylic acid which exists as a solid at room temperature and melts at 35° C. Sodium bicarbonate is generally a solid weak base which when protonated by an acid may decompose into $CO_2$. A $CO_2$ sensor was then exposed to a sequence of controls. First the sensor was exposed to air of an elevated temperature, then a sample of pure pivalic acid at elevated temperature. Then, the sensor was exposed to a sample of pivalic acid and sodium bicarbonate mixed in a stoichiometric ratio at room temperature. Finally, the sensor was exposed to a sample of a mixture of pivalic acid and sodium bicarbonate at an elevated temperature. When the sample reached the melting point of pivalic acid, the acid was converted into its liquid form, allowing for the reaction of pivalic acid with sodium bicarbonate and the subsequent release of $CO_2$. Of the various conditions, a sensor response was witnessed only when the pivalic acid sodium bicarbonate mixture was heated, demonstrating a controlled, triggered release of a volatile agent and its subsequent detection.

Exemplary Embodiments—Chemical Processes for Chemical Tag Release

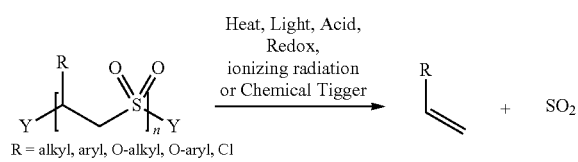

R = alkyl, aryl, O-alkyl, O-aryl, Cl

Triggered depolymerization of poly(vinyl sulfones) could directly release a chemical tag. The alkene can be detected or the R group in the alkene could have specific functionality that results in an easily detected signal. For example, if $R=CH_2C(CF_3)_2OH$ we could make use of the hydrogen bonding and acidity of the OH group to ensure a unique detection. Alternatively, if R=OEt or OAc then the alkene is very electron rich and also will have a unique chemical signature for detection. $SO_2$ release is also of interest and this gas has high reactivity with amines. It can also be readily oxidized in ambient atmosphere to create strong acids that can be easily chemically transduced.

Poly(alpha-methyl styrene) (Ar=Ph) is an example of a polymer that has a ceiling temperature of around 66° C. that is above room temperature but is much lower than its relative polystyrene (198° C.). With heating this polymer may readily depolymerize. The resultant alkene can function as a chemical tag. The phenyl ring could also have functionality attached to provide for a unique signal, or this material could be the matrix material that surrounds a chemical tag and its spontaneous depolymerization could result in a release of chemical tag.

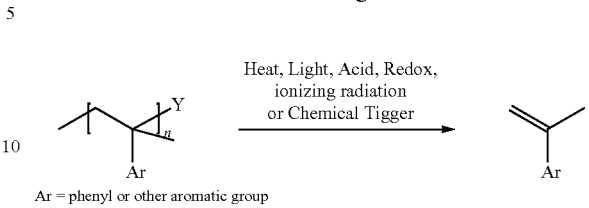

Ar = phenyl or other aromatic group

When the Ar group in these schemes is capable of absorbing light, it is also possible that these materials can be depolymerized photochemically.

Polyaldehydes are another class of polymers that will generally spontaneously depolymerize at elevated temperature. These polymerizations generally proceed by an ionic mechanism, but can also happen thermally. Formaldehyde (R=H) is a classic example and it spontaneously cyclizes and polymerizes. Heat treatment and moisture can release this molecule and it is sufficiently reactive to be easily detectable by a number of methods. Polyaldehydes can be chemically depolymerized and a simple acid trigger will generally give rise to depolymerization.

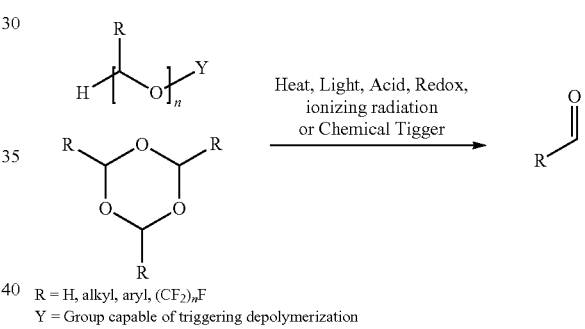

R = H, alkyl, aryl, $(CF_2)_nF$
Y = Group capable of triggering depolymerization In these schemes the terminal group, Y<attached to the oxygen can be a trigger. For example, if $Y=Si(i-Pr)_3$ then the depolymerization can be triggered by a process that cleaves the Si—O bond. Such a process can be trigged by strong base or fluoride ion. The released aldehydes can be designed to have unique properties. Fluorinated alkanes can produce aldehydes with electrophilic character that allow for unique detection. For example, these aldehydes may produce hemiacetals with alcohols or hydrate in the presence of water.

In addition to simple polyaldehydes, materials derived from aryl-ortho-dialdehydes can be readily depolymerized. The released monomers present unique chemical properties that can give rise to a distinct sensory signal.

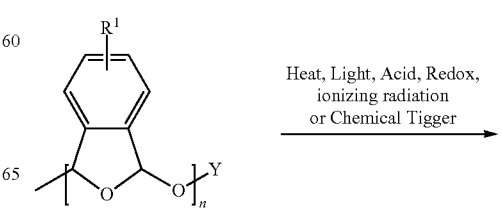

27
-continued

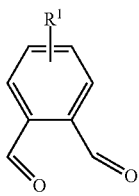

Many other established or existing depolymerization processes are possible and can be used as part of the chemical tag release encoding processes in this invention. For example, the process shown can be used to release reactive molecules that can go on to do further chemistry or be chemical tags.

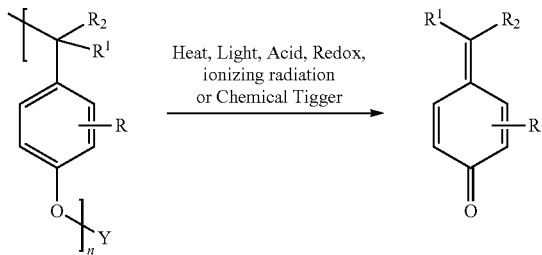

An exemplary advantage of depolymerization methods is, in some cases, a single event may give rise to many molecules for detection. This can allow for a strong signal that can be potentially triggered by a single event.

Thermal fragmentation is very common and is not limited to depolymerization processes. Any material if heated hot enough will generally begin to break into smaller fragments and this is understood from basic thermodynamics driven by a positive entropy gain. To illustrate the scope of this invention a number of different chemistries are suggested here that can be readily translated into easily detected signals.

Diels Alder reactions are reversible, and furan is particularly well known to in this regard. Furans are strongly electron donating molecules and can be detected photoluminescence quenching of chemiresistive methods. Similarly, the alkenes or alkynes that also fragment can be readily detected by known methods, including chemiresistors. Furans are generally electron donating molecules and the eliminated alkenes will generally most often be electron accepting compounds, thereby giving a complementary character for their detection.

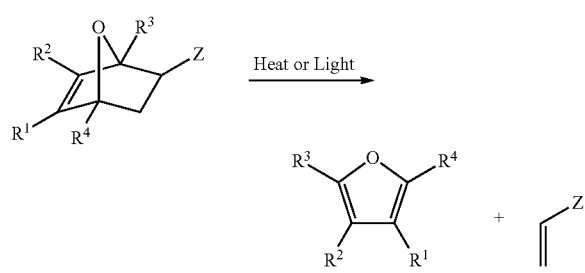

$R^{1-4}$ = H, alkyl, aryl
Z = $NO_2$, $CO_2R$, CN, OR, OAc, R

28
-continued

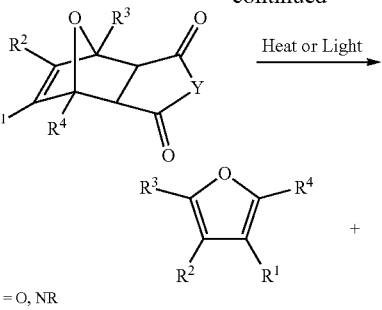

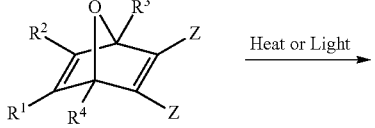

Y = O, NR

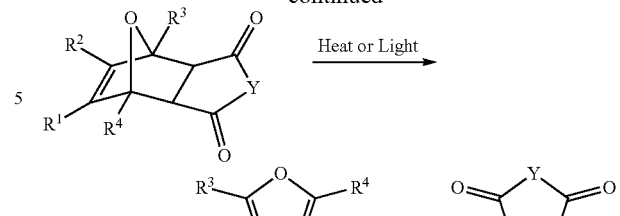

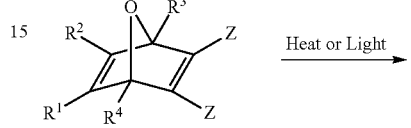

The retro or reverse Diels Alder reactions are not limited to generating furans, and can liberate dienes and other aromatic structures such as anthracenes. It may be advantageous to have one of the components be non-volatile either by virtue of its molecular weight of as a result of covalent connection to as surface, particle of polymer. These reactions will generally be most often initiated thermally, but can also be caused by light. Diels Alder reactions could also be used to thermally regulate the properties of polymers. For example, if a polymer is crosslinked by a Diels Alder reaction and this lowers the diffusion of chemical tags, thermal promotion of reverse Diels Alder reactions can be used to give an increase in the diffusion of the chemical tag or reagents associated with the generation of a chemical tag from a precursor material.

The forward Diels Alder reactions (as opposed to reverse Diels Alder reactions) can also be useful in liberating chemical tags and the examples given provide initial products that rapidly decompose to liberate carbon monoxide or sulfur dioxide. Methods are in hand for detection of both of these analytes with carbon nanotube chemical resistors. In the case of $SO_2$ the presence of air and moisture can result in the formation of strongly acidic materials that are also readily detected.

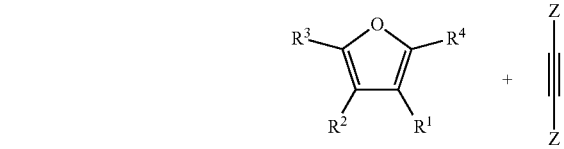

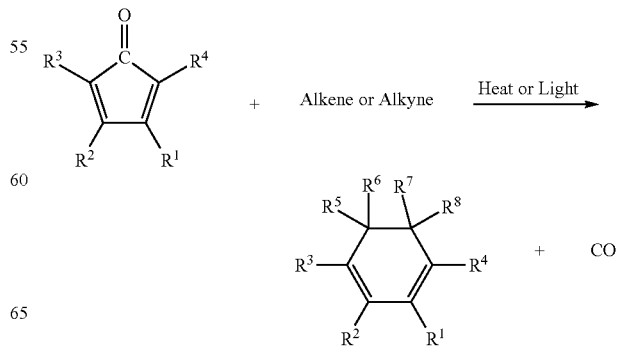

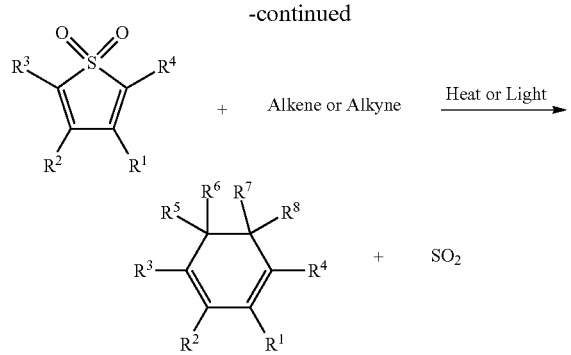

There are many other possible types of thermal or potentially photochemical processes that can give rise to chemical tags that are readily detectable. The eliminations shown below both give products that will generally be readily detectable. Eliminations that produce hydroxy amines are very attractive. The hydroxy amine group is an extremely strong electron donating molecule and will generally quench many fluorophores and will generally also donate electrons to a p-type semiconductive material, such as a carbon nanotube. The former would be recognized by a reduction in fluorescence from a sensory material and the latter would create an increase in resistance from a p-doped conductive semiconductive single walled carbon nanotube sensor. In the case that a $R^5SO_2H$ group is produced by an elimination, we can expect the detection of this material by virtue of its strong acidity. It is also possible to generate other acid groups, including carboxylates and halogen acids by thermal elimination. There are abundant fluorescent processes that give distinctive emission responses to strong acid. Additionally, carbon nanotubes are known to respond to acids and by placing other hydrogen accepting functionality on the surface of the carbon nanotubes, we can expect an enhanced signal. Acids are attractive signals to transduce as it is possible to create sensors that are activated to respond to materials of specific threshold acidities. Put differently we can imagine a sensor that is activated by a selector of a basicity that is insufficient to produce full proton transfer to create ionic species. Additionally, it is possible to make use of molecules that shift their electron affinity in response to protonation. Quinones are an example of molecules that have pH responsive electron affinities and we can expect that these molecules can be used to create redox quenching of emitters or carrier modulation in the semiconductors used in chemiresistive sensors.

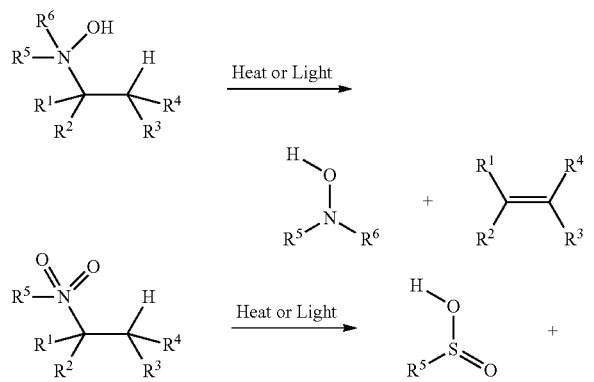

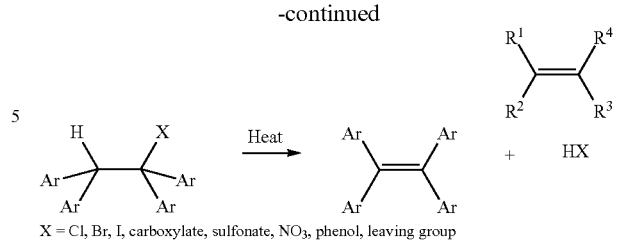

The alkenes generated in elimination reactions are similarly potential chemical tags. Chemiresistor methods exist for the selective detection of alkenes and the selectivity can be modulated by the choice of the substituents attached to the products generated by thermal elimination reactions.

Another type of thermal elimination that can be of use would be the elimination of a dihalogen such as shown. Similar processes can be imagined that produce, $I_2$ or IBr, or ICl. Dihalogens are strong oxidants and will generally quench most any emissive material and can be used to inject carriers into semiconductive materials. Carrier injection can result in a decrease in resistance in a chemiresitive sensor and would complement chemical tags that display the more common resistance increases resulting from the pinning, scattering, depleting of charge carriers. For example, such a response would be very distinct from the release of a donating furan or amine.

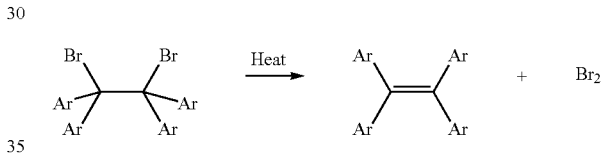

Many processes can be initiated by either heat or light. Photochemical processes generally require chromophores to be efficient. This can be illustrated by the following two examples, both of which can be thermally activated, however on the second example has a chromophore allowing photochemical activation. Both cases generate radical species that will generally be electronically active and readily transduced. The radicals generated will generally not persist in air and hence will generally rapidly dissipate. However, it is expected that the species will persist long enough for transient detection by a sensor.

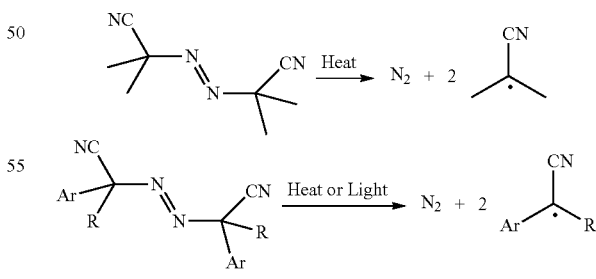

There are a number of other potential chemistries that can generate radical species that are expected to result in readily detectable signatures by sensors, including chemiresistors. The following examples are thermal processes that give rise to persistent radicals in addition to radicals that will generally likely only be transiently stable. The combination of these two electronically active materials can be used to create unique time dependent signals after triggered release. These examples will generally all be thermally triggerable, but direct photochemical activation will generally depend on the substituents.

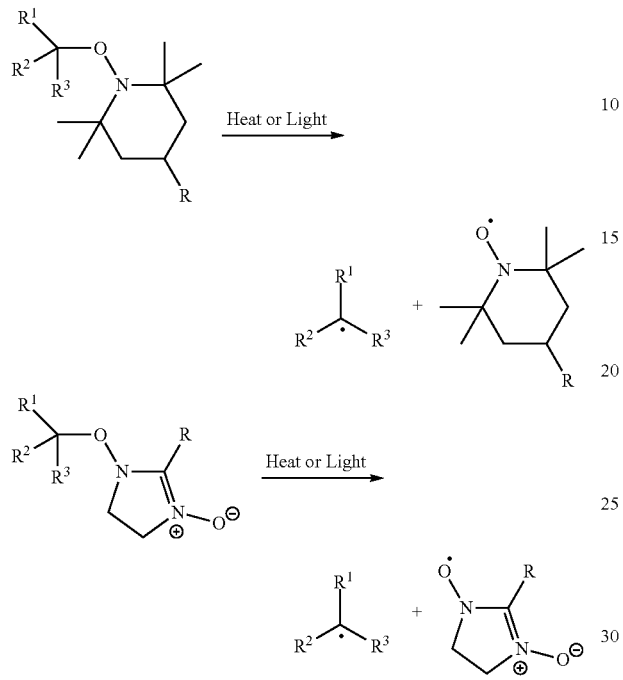

Oxygen centered radicals are particularly reactive and will generally be readily detected by a number of different sensing schemes, including chemiresistors. Peroxy groups can be thermally or photochemically activated. These materials can be volatile and detected in the case that the produces are not charged. The high reactivity of these groups can also be used to trigger other processes that indirectly create chemical tags.

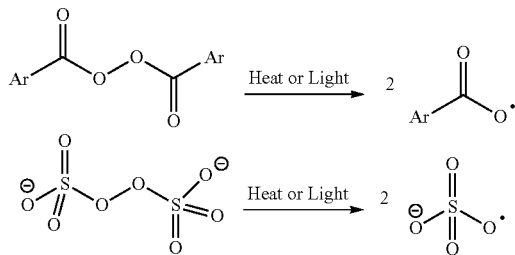

Thermal processes can also be used to decompose salts that are nominally non-volatile species to create neutral fragments that are volatile. A simple by effective example is the case of a carboxylate ammonium salt, which form the neutral vapors with thermal treatment.

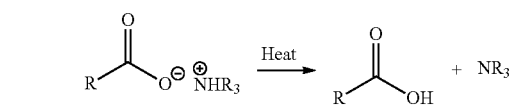

R = Ar, akyl, H, OR

The acid and the amine both offer detection opportunities. The basicity of the amine and acidity can be modulated by the choice of groups. For example, if R on the carboxylate is H, we generate formic acid, which can be readily detected by a carbon nanotube chemiresistive sensor. Similarly, aromatic amines are strongly donating and can be readily transduced. We expect that the substituents on the amine will generally be useful in creating unique responses. For example, by adding methyl groups as shown more strongly electron donating amines can be generated. In the case below the amine on the far right would be the stronger donor.

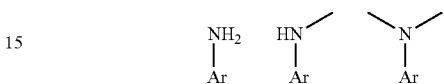

Thermal processes can be used to generate many different chemical signatures. For example, the following two processes can be used to generate oxidizing $I_2$ vapor of reducing NC—$BH_2$ groups in addition to Y species which could also be volatile. For example, Y could be an amine, ether, or thioether.

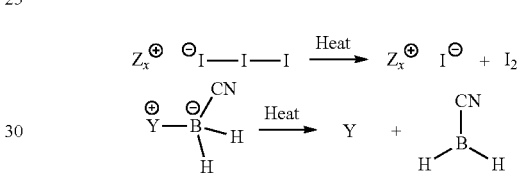

Changes caused by phase changes or photochemical processes can result in exposing a chemical tag precursor to water or an alcohol. $NO_2$—$NH_2$ catalytically decomposes to nitrous oxide, $N_2O$, when exposed to water. $N_2O$ is a relatively harmless gas used as a propellent in food containers and is known as laughing gas. $N_2O$ has a large chemical potential thereby allowing for unique detection capabilities. Anhydrides are thermally very stable but can react with either water or alcohols to release carboxylic acids for detection. In both cases the chemical tag release can be triggered by thermal or chemical methods. For example, a hydrated salt could be included in the chemical tag material that can be liberated by heat and cause the reaction. An alcohol could be physically separated in another material but activated to diffuse by a mechanical, photochemical, or thermal process and react to affect release of the chemical tag.

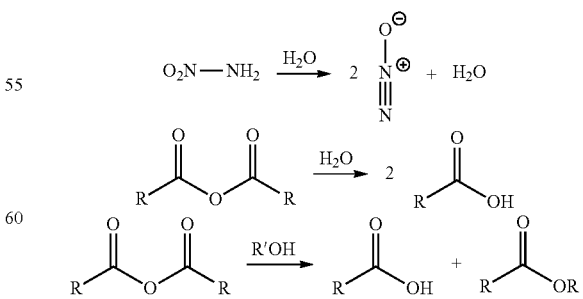

Photochemical methods offer a wide range of processes to release chemical tags and change the physical properties of materials. Oxides of nitrogen ($NO_x$) are readily detected and can also dissipate rapidly, allowing for transient signals. There are a number of direct and indirect methods by which different $NO_x$ species can be generated. Salts are not volatile and can be used to create authentication tags that last for extended periods. $NO_2^+$ and $NO^+$ cations can be indirectly photoreduced by placing a donor light emitting chromophore proximate to them. In this case an electron transfer occurs to create a new salt and release $NO_2$ and NO gas that can be readily detected by organic semiconducting materials. The wavelength of light for this activation process can be varied to give selective encoding and will generally be controlled by the dye.

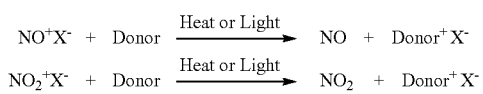

Direct photochemical generation of $NO_2$ and NO gas can be accomplished by irradiating the compounds shown. These processes generally require high energy UV light, but can also be thermally activated. There have been great advances in inexpensive light emitting diodes and other light sources that can be used to potentially create portable devices capable of photochemical generation of $NO_2$ and NO gas by this method.

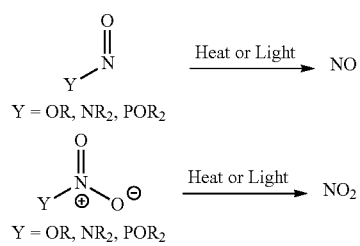

Nitroaromatic compounds are powerful electron acceptors that can be readily transduced either optically by the quenching of a sensor materials fluorescence of by charge transfer interactions with organic semiconductors. Polynitrated compounds form reversible complexes with amines and can be thermally liberated to generate a chemical tag signature.

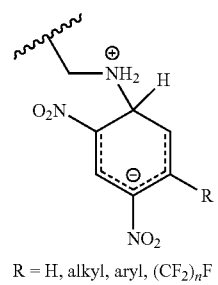

R = H, alkyl, aryl, $(CF_2)_nF$

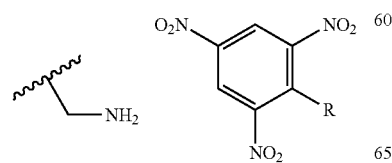

Photochemical methods can be used to generate persistent or transient acid species. Examples of photoacid generation are shown. In the case of the 2-naphthol species the acidity is only enhanced in the presence of light. However, with the iodonium and sulfonium salts photochemical methods result in an irreversible change that produces a persistent strong acid. The latter have been used in photolithography and a number of other processes.

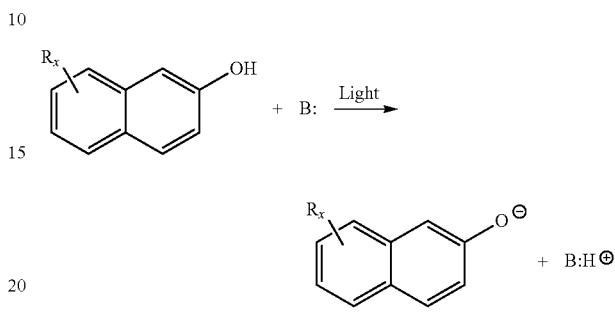

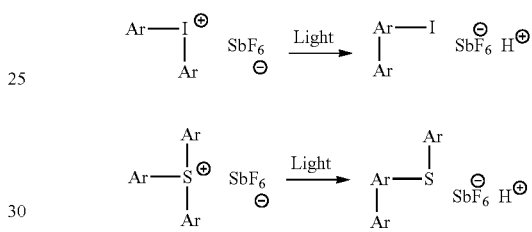

Photoacid generation can be used to modify the properties of a host material or liberate a chemical tag. The acid can produce catalytic processes such as the decomposition of a tert-butyl carbonate to release $CO_2$ and isobutylene, both of which can be detected by chemiresistive sensors.

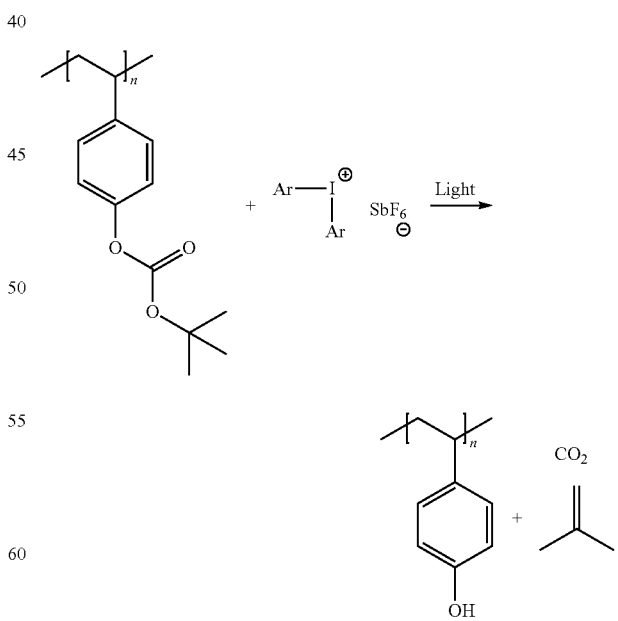

Photoacids can be used to trigger the depolymerization of aldehyde polymers as shown to give aldehydes that can be readily detected as chemical tags.

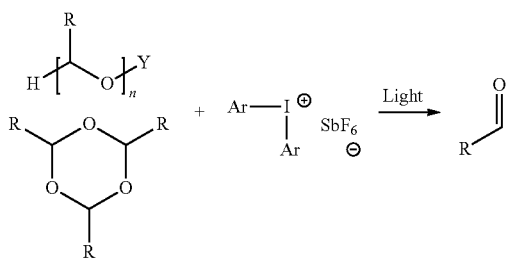

Photoacids can also catalyze hydrolysis reactions with acetals and esters. These processes can release phenols, carboxylic acids, carbonyls and alcohols all of which can be chemical tags. These reactions can also be used to modify the properties of a polymer that is modulating the physical separation of reagents of preventing diffusion of chemical tags or reactants that can produce chemical tags.

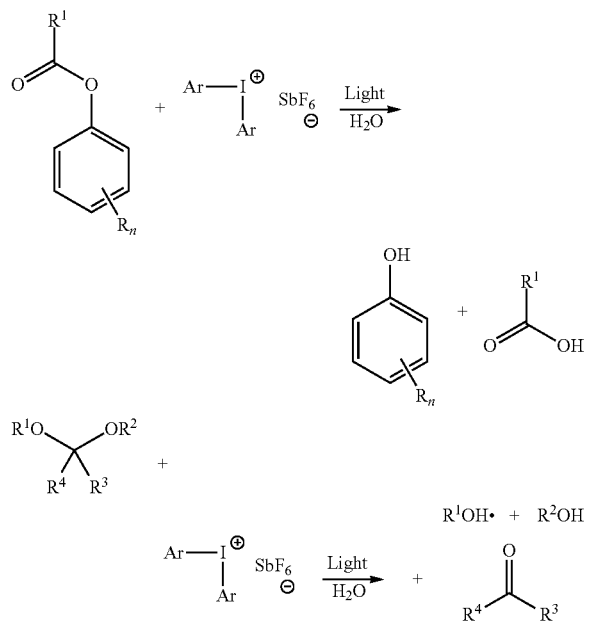

There are expansive opportunities to create chemical tag release/generation schemes based on photochemical processes. Photoinitiators and complex photoinitiation schemes have been developed that function at many different wavelengths. Photochemical processes are also used in biological imaging in the uncaging of emissive or reactive species. These methods could be used in the context of creating authentication tags. The reactive radicals generated in some of these schemes such as those shown could directly give chemical tags. Alternatively, these radicals can be used to initiate other processes that produce chemical tags.

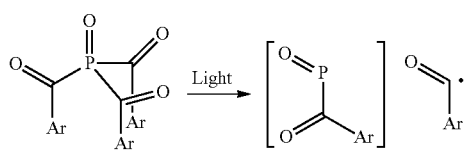

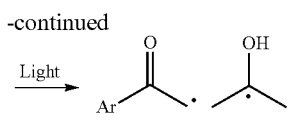

Many standard organic reactions could be converted into methods for the generation of readily transducable chemical tags. For example, N-bromosuccinimide is widely used to brominate allylic and benzylic C—H groups. HBr and $Br_2$ are generated in the mechanism, and both are easily and uniquely detectable potential chemical tags.

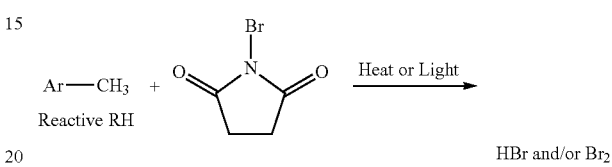

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. A label, comprising:
   the label associated with an article; and
   a chemical tag comprising a plurality of identifiable analytes, wherein a vapor signature of the plurality of identifiable analytes identifies a characteristic of the article, wherein the chemical tag is not inherently associated with the article,
   wherein the plurality of identifiable analytes do not comprise a fluorocarbon.

2. A label as in claim 1, wherein the label further comprises a marker comprising an optical barcode, watermark, hologram, RFID, invisible ink, dyes, colorimetric markers, fluorescent markers, nanoparticles, nanorods, quantum dots, antibodies, proteins, and/or nucleic acids.

3. A label as in claim 1, wherein the plurality of identifiable analytes comprises two or more types of functional groups within one or multiple molecules.

4. A label as in claim 1, wherein the chemical tag is applied at a plurality of spatially-distinct locations.

5. A system configured for identification of an article, comprising:
   a detector comprising a gas sensing component; and
   a label as in claim 1 associated with the article, the label comprising the chemical tag,
   wherein the detector is configured to determine the presence or absence of the chemical tag,
   wherein the detector signals a characteristic of the article upon exposure to the chemical tag, and
   wherein the chemical tag is not inherently associated with the article.

6. A system as in claim 5, wherein the label comprises a second identifiable component.

7. A system as in claim 6, wherein the second identifiable component comprises an optical barcode, hologram, watermark, RFID, invisible ink, dyes, colorimetric markers, fluorescent markers, nanoparticles, nanorods, quantum dots, antibodies, proteins, nucleic acids, or combinations thereof.

* * * * *